US00PP15063P2

(12) United States Plant Patent
Scorza

(10) Patent No.: US PP15,063 P2
(45) Date of Patent: Aug. 3, 2004

(54) PEACH TREE NAMED 'SWEET-N-UP'

(50) Latin Name: *Prunus persica*
Varietal Denomination: Sweet-N-UP

(75) Inventor: Ralph Scorza, Shepherdstown, WV (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/984,543

(22) Filed: Oct. 30, 2001

(51) Int. Cl.[7] ..... A01H 5/00
(52) U.S. Cl. ..... Plt./198
(58) Field of Search ..... Plt./198

*Primary Examiner*—Anne Marie Grunberg
(74) *Attorney, Agent, or Firm*—John D. Fado; Evelyn M. Rabin

(57) ABSTRACT

A new and distinct variety of peach called 'Sweet-N-UP' is characterized by an upright tree growth form suitable for standard-density and high-density plantings. Fruit is yellow, melting-flesh of excellent dessert-quality flavor, and of large size with approximately 80% red blush over a yellow ground color.

3 Drawing Sheets

BACKGROUND OF THE NEW VARIETY

The present invention relates to a new and distinct variety of peach tree [*Prunus persica* (L.) Batsch] which is named 'Sweet-N-UP'.

The new variety is attractive commercially for its upright tree form, productivity and for fruit of excellent quality. It may be utilized in standard- and high-density plantings.

The new variety was originated at the Appalachian Fruit Research Station, Agricultural Research Service, U.S. Department of Agriculture in Kearneysville, W. Va. and was identified as KV930278. It resulted from hand pollination of peach seedling identified as KV882304 (unpatented) with pollen from peach seedling identified as BO87021003 (unpatented). KV882304 resulted from hand pollination of 'Bounty' (unpatented) peach with pollen of "pillar" peach. BO87021003 resulted from a cross of 'Firered'×"pillar". "Pillar" or "broomy" peach trees were originally reported from Japan as columnar trees used as ornamentals. The "pillar" pollen used in these crosses was obtained from Italy and is not patented. BO87021003 was obtained from the University of Bologna, Bologna, Italy.

Plants of the new variety were selected in 1996 from a group of 358 seedlings produced from the pollination described hereinabove. The original 'Sweet-N-UP' tree has maintained its upright form, high fruit quality and productivity for 6 years. The plant was asexually propagated through grafting on to 'Lovell' seedling rootstock. Asexual propagation through bud grafting was carried out at Adams County Nursery, Aspers, Pa., the budwood provided under a Material Transfer Agreement. Buds of 'Sweet-N-UP' were grafted onto 'Lovell', a widely used rootstock of standard tree growth habit, following standard bud-grafting techniques. Following one year of growth in the nursery, these grafted trees were dug and transferred to their permanent orchard location following standard techniques. A total of 96 bud-grafted 'Sweet-N-UP' trees were planted in a replicated block orchard design with 12 treatment blocks, each containing 8 trees. Trees were spaced at 1.5 m, 2 m, 4 m or 6 m within rows, and 6 m between rows. Half of the trees were pruned to one leader (one major limb) and half to multileader (3 major limbs). These trees were tested in this planting for 3 years and have maintained their tree form, high fruit quality and productivity. No aberrant types have appeared in these plantings developed through vegetative propagation, demonstrating the stability of the new variety. The plant is self-fertile.

The new variety is distinct from its parents in its combination of high fruit quality and upright growth habit. It is distinguished from its parents by its superior fruit quality: fruit are larger, firmer and with more red skin color than fruit of either parent. It is distinguished from other commercial peach varieties by a distinctly upright growth habit with branch angles from the main axis at approximately 42–51°, in contrast to branch angles of standard peach trees which average approximately 60°. Fruit have a distinct combination of large size, firmness and red skin color.

Fruit are melting-flesh, dessert type, yellow, flavorful and firm until full-ripe. Fruit size averages 73–77 mm in diameter and 217 g in weight. Fruit are sweet with a good balance of acidity. Brix of firm-ripe fruit averages between 11.5 and 13°, depending on date of harvest and environment. Fruit maintains firmness on the tree and in storage at levels comparable to or exceeding current commercial peach cultivars.

SUMMARY OF THE NEW VARIETY

The new and distinct variety of peach tree is productive and vigorous with an upright growth habit. The fruit is large in size, is freestone and of excellent eating quality. The fruit has yellow melting-flesh with approximately 80% red blush over a yellow ground color.

Figure 1:
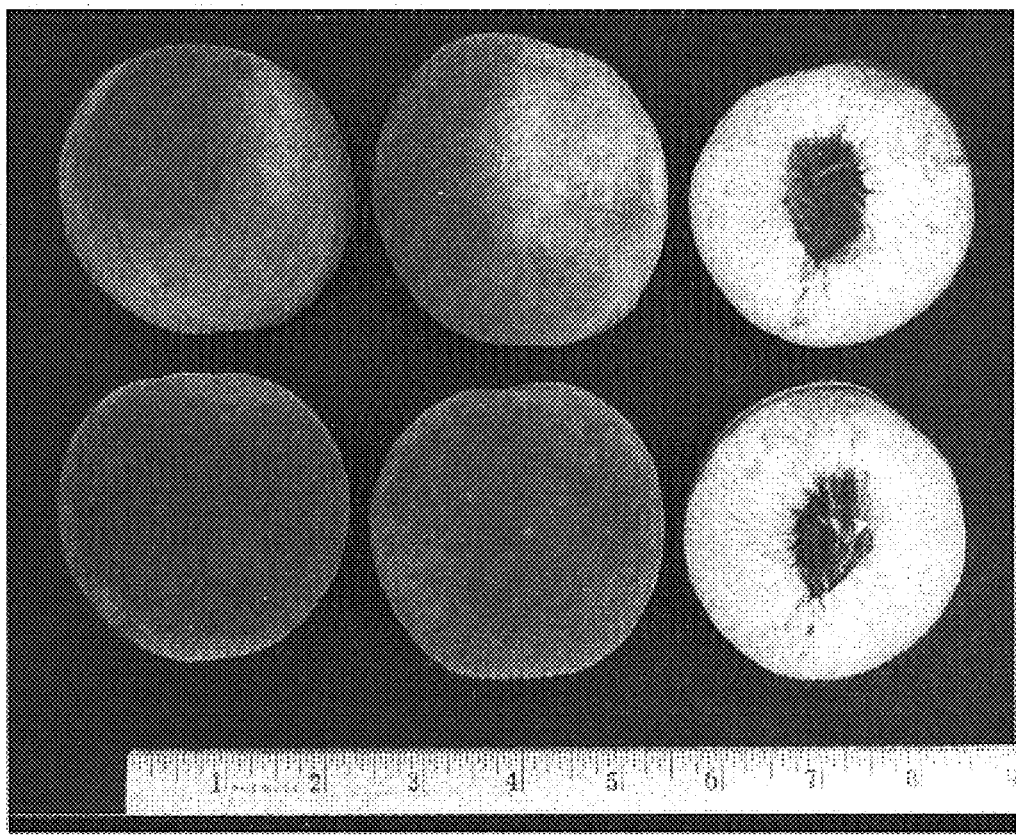
FIG. 1 is a photograph of the fruit of 'Sweet-N-UP' peach in full color showing the ripe fruit viewed in profile and sectioned in half from end to end, with one one-half of the fruit shown with the stone in place in the flesh.
Figure 2:
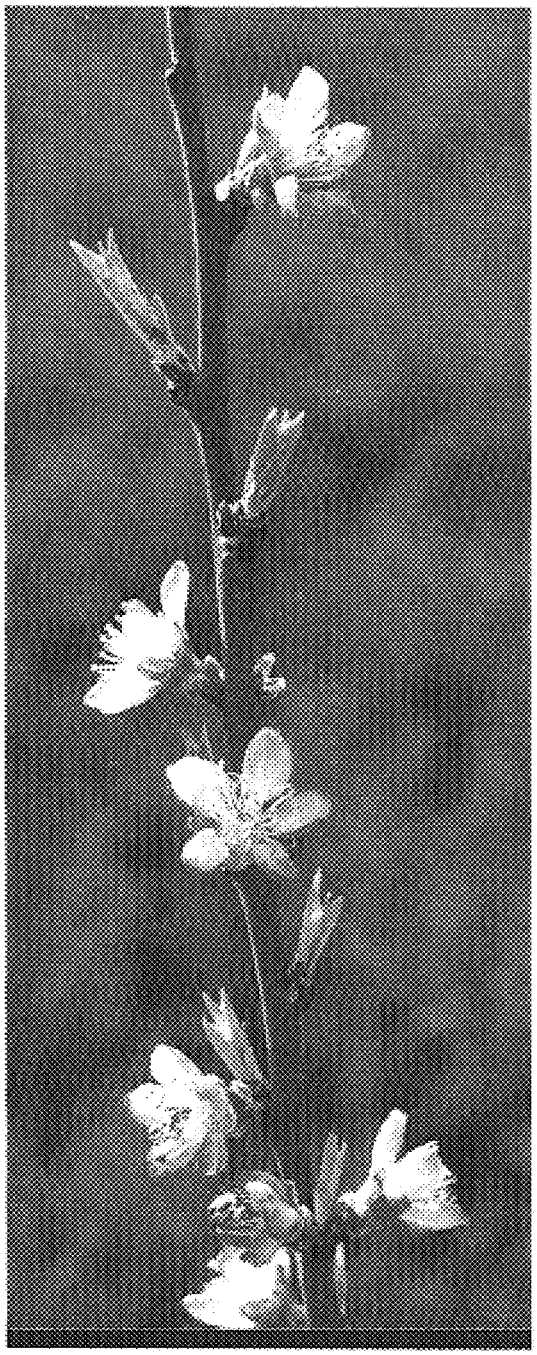
FIG. 2 is a photograph of a representative stem of 'Sweet-N-UP' peach flowers in full color.
Figure 3:
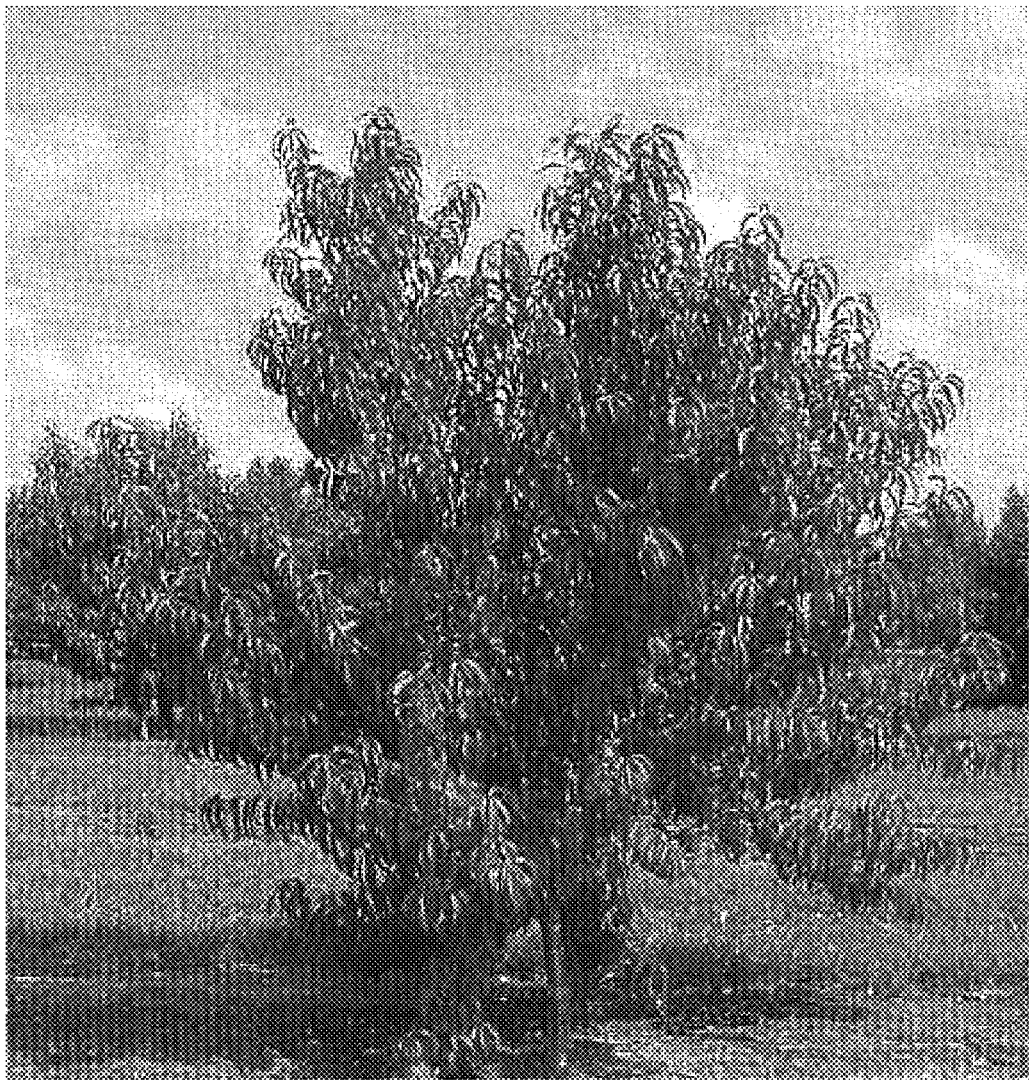
FIG. 3 is a photograph of a fruiting tree of 'Sweet-N-UP' peach, grafted on to 'Lovell' seedling rootstock, after 2 growing seasons, showing upright form of tree architecture and fruit production.

The figures show photographs in color as accurate as reasonably possible to attain in color photographic reproductions of this type.

DETAILED DESCRIPTION OF THE NEW VARIETY

The following is a detailed description of the botanical and pomological characteristics of the subject peach. Color data are presented in The Royal Horticultural Society (R.H.S.) Colour Chart designations. Where dimensions, sizes, color, and other characteristics are given, it is to be understood that such characteristics are approximations of averages set forth as accurately as practicable.

The descriptions reported herein are from specimens grown at Kearneysville, W. Va.

Tree:

*Size/vigor.*—Canopy size at 2 years — height 3.3 m, width 2.0 m, depth 2.0 m compared with a standard tree ('Harrow Beauty') control at 2.8, 2.1, and 2.3 m, respectively; average 41 cm of seasonal short growth from previous season growth on 5-year-old trees.

*Growth.*—Upright with branch angles from the main axis averaging approximately 42–50°.

*Density.*—Medium dense to dense.

*Productivity.*—After 2 years in the field, 2.1 kg/tree compared with standard control ('Harrow Beauty') at 1.2 kg/tree.

*Bearing.*—Regular.

*Disease resistance.*—Not determined.

Trunk:

*Size.*—Circumference — 21.7 cm at 2 years on 'Lovell' rootstock with standard tree ('Harrow Beauty') at 19.6 cm.

*Color.*—Brown ranging from RHS 201 B to C.

*Trunk lenticel density.*—7/mm$^2$.

*Trunk lenticel color.*—RHS 164B.

*Trunk lenticel size.*—6 mm long.

Branches:

*Size.*—One-year branch diameter — 17.0 mm; 2-year branch diameter — 20.4 mm.

*Texture.*—Smooth to medium rough; varies with maturity.

*Color.*—Ranging from RHS 166 A to B.

*Branch crotch angles.*—42–50°.

Leaves:

*Size.*—Average length — 15.7 cm, average width — 4.3 cm.

*Texture.*—Glabrous.

*Margin.*—Crenate to serrulate.

*Form.*—Lancelolate, pointed.

*Petiole.*—Length — 10.7 mm, width — 1.7 mm, thickness — 1.6 mm; color RHS 151C.

*Glands.*—Reniform; located on base of leaf and upper portion of the petiole; length — 1.0 mm; average 4/leaf, varying from 1 to 6.

*Color.*—Upper surface RHS 137A; lower surface RHS 137C.

Flowers:

*Petal size.*—12×10 mm.

*Bloom period.*—Variable depending on weather; late March to mid-April in Eastern Panhandle of West Virginia.

*Color.*—Petals ranging from RHS 65 A to B, anthers RHS 14B.

*Pollen.*—Present; self-fertile, no pollinator required; color RHS 14C.

*Description.*—Flowers are complete, perfect, perigynous; sepals (5) form a hypanthium cup; petals (5) are attached to hypanthium; stamens are attached to interior of hypanthium at or below rim of hypanthium cup; pistil (1) is superior averaging; no detectable scent.

Fruit:

*Maturity when described.*—Shipping ripe to eating ripe.

*Average date of harvest.*—Late July to early August in Kearneysville, W. Va.

*Size.*—Large; average diameter axially 73–77 mm depending on crop load and environment.

*Fruit pedicel color.*—RHS N144D.

Flesh:

*Ripens.*—Evenly.

*Texture.*—Firm; slope of softening over 14 days using electronic impact sensor — 0.71[1] compared with — 0.62 for standard cultivar 'O'Henry' ([1]Meredith et al. 1990. *Transactions ASAE,* vol. 33, pp. 186–188).

*Fibers.*—Small, few, tender.

*Juice.*—Moderate.

*Aroma.*—Moderate.

*Flavor.*—Very good.

*Eating quality.*—Very good; average brix of 11.5 to 13° depending upon date of harvest and environmental conditions.

*Flesh color.*—RHS ranging from 16 C to 16D.

*Pit cavity color.*—RHS 34A; proximal to the stone, RHS ranging from 53C to 53D.

Skin:

*Thickness.*—Medium.

*Tendency to crack.*—None.

*Down.*—Moderate; short in length.

*Color.*—Blush (overcolor) ranges from RHS N77A to 34B to 34C; ground (undercolor) RHS 10A.

Stone:

*Type.*—Freestone.

*Size.*—Medium; average length 36.6 mm, average width 25.7 mm, average thickness 18.4 mm.

*Form.*—Obovate.

*Tendency to split.*—Six–14% stone splitting depending on environmental conditions.

*Color.*—RHS 166 C.

I claim:

1. A new and distinct variety of peach tree, substantially as illustrated and described.

* * * * *